United States Patent
Johnson et al.

(10) Patent No.: US 11,815,311 B2
(45) Date of Patent: *Nov. 14, 2023

(54) LYOPHILIZATION CONTAINER FILL FIXTURE, SYSTEM AND METHOD OF USE

(71) Applicant: Terumo BCT Biotechnologies, LLC, Lakewood, CO (US)

(72) Inventors: Nathaniel T. Johnson, Highlands Ranch, CO (US); Rylan A. Summit, Denver, CO (US); Dennis A. Bridges, Arvada, CO (US); Dennis J. Hlavinka, Arvada, CO (US); Kestas P. Parakininkas, Englewood, CO (US); Kirk L. Weimer, Green Valley, AZ (US); Michael Lawrence Glover, Lakewood, CO (US); Alexander Du Nguyen, Denver, CO (US); Margaret V. Kwiat, Evergreen, CO (US)

(73) Assignee: Terumo BCT Biotechnologies, LLC, Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/903,506

(22) Filed: Sep. 6, 2022

(65) Prior Publication Data

US 2023/0008773 A1 Jan. 12, 2023

Related U.S. Application Data

(63) Continuation of application No. 16/815,904, filed on Mar. 11, 2020, now Pat. No. 11,609,043.

(Continued)

(51) Int. Cl.
*F26B 5/06* (2006.01)
*A61M 1/02* (2006.01)
(Continued)

(52) U.S. Cl.
CPC .............. *F26B 5/06* (2013.01); *A01N 1/0263* (2013.01); *A01N 1/0284* (2013.01);
(Continued)

(58) Field of Classification Search
CPC .... F26B 5/00; F26B 5/06; F26B 21/14; F26B 25/063; F26B 25/18; F26B 3/30;
(Continued)

(56) References Cited

U.S. PATENT DOCUMENTS

| 136,036 A | 2/1873 | Craven |
| 1,441,570 A | 1/1923 | Fitzgerald |

(Continued)

FOREIGN PATENT DOCUMENTS

| AU | 517248 B2 | 7/1981 |
| AU | 590193 B2 | 11/1989 |

(Continued)

OTHER PUBLICATIONS

US 8,359,766 B2, 01/2013, Hubbard et al. (withdrawn)

(Continued)

*Primary Examiner* — Stephen M Gravini
(74) *Attorney, Agent, or Firm* — Harness, Dickey & Pierce, P.L.C.

(57) ABSTRACT

Provided is a gas fill fixture for use in lyophilization, a related system and method. The gas fill fixture includes a chassis, fill indicator and a lid, such that the chassis and lid together form a cavity for receiving a flexible lyophilization container. The system includes a lyophilization container, a lyophilizer and a gas fill fixture incorporating a chassis, a fill indicator and a lid. The method includes process steps for using the system to lyophilize a fluid.

20 Claims, 7 Drawing Sheets

Related U.S. Application Data

(60) Provisional application No. 62/971,072, filed on Feb. 6, 2020, provisional application No. 62/952,752, filed on Dec. 23, 2019, provisional application No. 62/818,214, filed on Mar. 14, 2019.

(51) Int. Cl.
  *A01N 1/02* (2006.01)
  *A61J 1/10* (2006.01)
  *F26B 21/14* (2006.01)
  *A61J 1/14* (2023.01)
  *B65D 51/24* (2006.01)
  *F26B 25/06* (2006.01)
  *F26B 25/18* (2006.01)

(52) U.S. Cl.
  CPC ............. *A01N 1/0289* (2013.01); *A61J 1/10* (2013.01); *A61M 1/0277* (2014.02); *F26B 21/14* (2013.01); *A01N 1/0252* (2013.01); *A61J 1/1468* (2015.05); *A61M 2202/0415* (2013.01); *A61M 2205/3389* (2013.01); *A61M 2205/584* (2013.01); *B65D 51/241* (2013.01); *F26B 25/063* (2013.01); *F26B 25/18* (2013.01)

(58) Field of Classification Search
  CPC ........ A61M 1/0277; A61M 2202/0415; A61M 2205/3389; A01N 1/0289; A01N 1/0263; A01N 1/0284; A01N 1/0252; A61J 1/10; A61J 1/1468; A61J 1/2093
  USPC .............................................. 34/284, 296, 92
  See application file for complete search history.

(56) References Cited

U.S. PATENT DOCUMENTS

| | | |
|---|---|---|
| 1,504,225 A | 8/1924 | Fitzgerald |
| 1,956,784 A | 5/1934 | Allen |
| 2,659,986 A | 11/1953 | Hink, Jr. |
| 2,704,075 A | 3/1955 | Cherkin |
| 2,767,117 A | 10/1956 | Crawley |
| 2,893,843 A | 7/1959 | Adams, Jr. |
| 2,912,359 A | 11/1959 | Anigstein et al. |
| 3,008,879 A | 11/1961 | Harvill |
| 3,024,167 A | 3/1962 | Damaskus |
| 3,057,781 A | 10/1962 | Mace et al. |
| 3,123,443 A | 3/1964 | Smeby |
| 3,187,750 A | 6/1965 | Tenczar |
| 3,223,593 A | 12/1965 | Aldrich et al. |
| 3,228,841 A | 1/1966 | Cohen et al. |
| 3,229,813 A | 1/1966 | Crowe, Jr. et al. |
| 3,236,732 A | 2/1966 | Arquilla |
| 3,247,957 A | 4/1966 | Kemble |
| 3,260,648 A | 7/1966 | Fox |
| 3,294,523 A | 12/1966 | Morningstar |
| 3,322,634 A | 5/1967 | Fulthorpe |
| 3,375,824 A | 4/1968 | Krakauer et al. |
| 3,395,210 A | 7/1968 | Lenahan et al. |
| 3,423,290 A | 1/1969 | Chappelle |
| 3,453,180 A | 7/1969 | Fraser, Jr. et al. |
| 3,466,249 A | 9/1969 | Anderson |
| 3,468,471 A | 9/1969 | Linder |
| 3,490,437 A | 1/1970 | Bakondy et al. |
| 3,519,572 A | 7/1970 | Kita |
| 3,533,934 A | 10/1970 | Armanini |
| 3,537,189 A | 11/1970 | Bender et al. |
| 3,548,051 A | 12/1970 | Dingwall Hamilton |
| 3,556,760 A | 1/1971 | Bender et al. |
| 3,565,987 A | 2/1971 | Schuurs |
| 3,571,940 A | 3/1971 | Bender |
| 3,573,063 A | 3/1971 | Williams |
| 3,574,950 A | 4/1971 | Dantoni |
| 3,607,858 A | 9/1971 | Querry et al. |
| 3,627,878 A | 12/1971 | Linsner |
| 3,629,142 A | 12/1971 | Marbach |
| 3,674,860 A | 7/1972 | Welter et al. |
| 3,714,345 A | 1/1973 | Hirata |
| 3,717,708 A | 2/1973 | Wada et al. |
| 3,730,843 A | 5/1973 | McKie, Jr. |
| 3,799,740 A | 3/1974 | Mincey |
| 3,803,299 A | 4/1974 | Nouel |
| 3,831,293 A | 8/1974 | Ingram et al. |
| 3,859,047 A | 1/1975 | Klein |
| 3,922,145 A | 11/1975 | Turner et al. |
| 3,932,943 A | 1/1976 | Briggs et al. |
| 3,944,665 A | 3/1976 | Galoian et al. |
| 3,945,523 A | 3/1976 | Wertlake et al. |
| 3,964,865 A | 6/1976 | Das |
| 3,973,002 A | 8/1976 | Hagan et al. |
| 3,987,159 A | 10/1976 | Spona et al. |
| 3,993,585 A | 11/1976 | Pinto et al. |
| 4,001,944 A | 1/1977 | Williams |
| 4,002,739 A | 1/1977 | Turner et al. |
| 4,035,924 A | 7/1977 | Faure |
| 4,045,176 A | 8/1977 | Proksch et al. |
| 4,049,673 A | 9/1977 | Scheinberg |
| 4,056,484 A | 11/1977 | Heimburger et al. |
| 4,059,491 A | 11/1977 | Iwasa et al. |
| 4,080,265 A | 3/1978 | Antonik |
| 4,089,944 A | 5/1978 | Thomas |
| 4,109,396 A | 8/1978 | Fraser |
| 4,127,502 A | 11/1978 | Li Mutti et al. |
| 4,134,943 A | 1/1979 | Knitsch et al. |
| 4,141,856 A | 2/1979 | Dorwart, Jr. et al. |
| 4,141,887 A | 2/1979 | Seufert |
| 4,155,186 A | 5/1979 | Robinson |
| 4,157,383 A | 6/1979 | Sedlacek et al. |
| 4,188,318 A | 2/1980 | Shanbrom |
| 4,189,400 A | 2/1980 | Proksch et al. |
| 4,202,665 A | 5/1980 | Wenz et al. |
| 4,218,321 A | 8/1980 | Sasaki et al. |
| 4,249,826 A | 2/1981 | Studievic et al. |
| 4,284,725 A | 8/1981 | Fennel, III et al. |
| 4,287,087 A | 9/1981 | Brinkhous et al. |
| 4,298,441 A | 11/1981 | Seidel et al. |
| 4,323,478 A | 4/1982 | Adams et al. |
| 4,324,685 A | 4/1982 | Louderback |
| 4,330,463 A | 5/1982 | Luijerink |
| 4,333,767 A | 6/1982 | Nass |
| 4,337,240 A | 6/1982 | Saklad |
| 4,442,655 A | 4/1984 | Stroetmann |
| 4,456,590 A | 6/1984 | Rubinstein |
| 4,465,774 A | 8/1984 | Huang et al. |
| 4,495,278 A | 1/1985 | Thomas |
| 4,506,455 A | 3/1985 | Rossi |
| 4,543,335 A | 9/1985 | Sommer et al. |
| 4,581,231 A | 4/1986 | Purcell et al. |
| 4,595,021 A | 6/1986 | Shimizu et al. |
| 4,614,795 A | 9/1986 | Chavin et al. |
| 4,624,927 A | 11/1986 | Fukushima et al. |
| 4,650,678 A | 3/1987 | Fuhge et al. |
| 4,664,913 A | 5/1987 | Mielke et al. |
| 4,666,725 A | 5/1987 | Yamashita et al. |
| 4,687,664 A | 8/1987 | Philapitsch et al. |
| 4,716,119 A | 12/1987 | Rehner et al. |
| 4,722,790 A | 2/1988 | Cawley et al. |
| 4,730,460 A | 3/1988 | Coelho et al. |
| 4,731,330 A | 3/1988 | Hill et al. |
| 4,746,730 A | 5/1988 | De Ambrosi et al. |
| 4,780,314 A | 10/1988 | Graves |
| 4,806,343 A | 2/1989 | Carpenter et al. |
| 4,812,557 A | 3/1989 | Yasushi et al. |
| 4,813,210 A | 3/1989 | Masuda et al. |
| 4,850,353 A | 7/1989 | Stasz et al. |
| 4,874,690 A | 10/1989 | Goodrich, Jr. et al. |
| 4,877,608 A | 10/1989 | Lee et al. |
| 4,877,741 A | 10/1989 | Babcock et al. |
| 4,902,287 A | 2/1990 | Carmen et al. |
| 4,904,641 A | 2/1990 | Eibl et al. |
| 4,973,327 A | 11/1990 | Goodrich, Jr. et al. |
| 4,986,998 A | 1/1991 | Yoo et al. |
| 4,994,057 A | 2/1991 | Carmen et al. |
| 5,043,261 A | 8/1991 | Goodrich et al. |

(56) References Cited

U.S. PATENT DOCUMENTS

| | | |
|---|---|---|
| 5,045,446 A | 9/1991 | Goodrich, Jr. et al. |
| 5,059,036 A | 10/1991 | Richison et al. |
| 5,059,518 A | 10/1991 | Kortright et al. |
| 5,061,789 A | 10/1991 | Moller et al. |
| 5,063,178 A | 11/1991 | Toomey |
| 5,073,378 A | 12/1991 | Shoshan et al. |
| 5,114,004 A | 5/1992 | Isono et al. |
| 5,118,795 A | 6/1992 | Rubinstein |
| 5,129,162 A | 7/1992 | Hemmersbach et al. |
| 5,147,803 A | 9/1992 | Enomoto |
| 5,151,500 A | 9/1992 | Wismer-Pedersen et al. |
| 5,171,661 A | 12/1992 | Goodrich, Jr. et al. |
| 5,178,884 A | 1/1993 | Goodrich et al. |
| 5,213,814 A | 5/1993 | Goodrich, Jr. et al. |
| 5,242,792 A | 9/1993 | Rudolph et al. |
| 5,257,983 A | 11/1993 | Garyantes et al. |
| 5,260,420 A | 11/1993 | Burnouf-Radosevich et al. |
| 5,262,325 A | 11/1993 | Zimmermann et al. |
| 5,304,383 A | 4/1994 | Eibl et al. |
| 5,309,649 A | 5/1994 | Bergmann et al. |
| 5,340,592 A | 8/1994 | Goodrich, Jr. et al. |
| 5,399,670 A | 3/1995 | Bhattacharya et al. |
| 5,411,893 A | 5/1995 | Eden et al. |
| 5,420,250 A | 5/1995 | Lontz |
| 5,425,951 A | 6/1995 | Goodrich, Jr. et al. |
| 5,464,471 A | 11/1995 | Whalen et al. |
| 5,514,123 A | 5/1996 | Adolf et al. |
| 5,514,586 A | 5/1996 | Hottinger et al. |
| 5,527,260 A | 6/1996 | Kameyama |
| 5,547,873 A | 8/1996 | Magneson et al. |
| 5,551,781 A | 9/1996 | Wilkes et al. |
| 5,585,007 A | 12/1996 | Antanavich et al. |
| 5,637,345 A | 6/1997 | Lee et al. |
| 5,648,206 A | 7/1997 | Goodrich, Jr. et al. |
| 5,651,966 A | 7/1997 | Read et al. |
| 5,656,498 A | 8/1997 | Iijima et al. |
| 5,690,963 A | 11/1997 | Spargo et al. |
| 5,695,764 A | 12/1997 | Bontemps |
| 5,698,535 A | 12/1997 | Geczy et al. |
| 5,736,313 A | 4/1998 | Spargo et al. |
| 5,747,268 A | 5/1998 | Herring et al. |
| 5,750,330 A | 5/1998 | Tometsko et al. |
| 5,750,657 A | 5/1998 | Edwardson et al. |
| 5,759,774 A | 6/1998 | Hackett et al. |
| 5,795,571 A | 8/1998 | Cederholm-Wlliams et al. |
| 5,831,027 A | 11/1998 | McIntosh et al. |
| 5,834,418 A | 11/1998 | Brazeau et al. |
| 5,837,519 A | 11/1998 | Savage et al. |
| 5,849,473 A | 12/1998 | Cabrera et al. |
| 5,853,388 A | 12/1998 | Semel |
| 5,860,222 A | 1/1999 | Leander |
| 5,861,311 A | 1/1999 | Maples et al. |
| 5,891,393 A | 4/1999 | Read et al. |
| 5,919,766 A | 7/1999 | Osterberg et al. |
| 5,919,935 A | 7/1999 | Platz et al. |
| 5,928,213 A | 7/1999 | Barney et al. |
| 5,946,931 A | 9/1999 | Lomax et al. |
| 5,968,831 A | 10/1999 | Shukla et al. |
| 5,985,582 A | 11/1999 | Triscott |
| 6,007,529 A | 12/1999 | Gustafsson et al. |
| 6,034,060 A | 3/2000 | Yamamoto et al. |
| 6,060,233 A | 5/2000 | Wiggins |
| 6,132,454 A | 10/2000 | Fellows |
| 6,139,878 A | 10/2000 | Summaria et al. |
| 6,148,536 A | 11/2000 | Iijima |
| 6,187,553 B1 | 2/2001 | Antignani et al. |
| 6,199,297 B1 | 3/2001 | Wisniewski |
| 6,218,195 B1 | 4/2001 | Gottschalk et al. |
| 6,221,575 B1 | 4/2001 | Roser et al. |
| 6,270,985 B1 | 8/2001 | Gottschalk et al. |
| 6,323,036 B1 | 11/2001 | Chapoteau et al. |
| 6,323,037 B1 | 11/2001 | Lauto et al. |
| 6,331,557 B1 | 12/2001 | Brugnara et al. |
| 6,346,216 B1 | 2/2002 | Kent |
| 6,350,584 B1 | 2/2002 | Gottschalk et al. |
| 6,358,236 B1 | 3/2002 | DeFoggi et al. |
| 6,358,678 B1 | 3/2002 | Bakaltcheva et al. |
| 6,372,423 B1 | 4/2002 | Braun |
| 6,381,870 B1 | 5/2002 | Kohlman et al. |
| 6,398,771 B1 | 6/2002 | Gustafsson et al. |
| 6,416,717 B1 | 7/2002 | Suzuki et al. |
| 6,472,162 B1 | 10/2002 | Coelho et al. |
| 6,517,526 B1 | 2/2003 | Tamari |
| 6,566,504 B2 | 5/2003 | Bhattacharya et al. |
| 6,608,237 B1 | 8/2003 | Li et al. |
| RE38,431 E | 2/2004 | Miekka et al. |
| 6,773,425 B1 | 8/2004 | Tamari |
| 6,852,540 B2 | 2/2005 | Makiuchi et al. |
| 6,869,901 B2 | 3/2005 | Lubker, II |
| 6,872,576 B1 | 3/2005 | McIntyre |
| 6,887,852 B1 | 5/2005 | Paik et al. |
| 6,890,512 B2 | 5/2005 | Roser et al. |
| 6,981,337 B2 | 1/2006 | Jones et al. |
| 7,041,635 B2 | 5/2006 | Kim et al. |
| 7,048,709 B2 | 5/2006 | Goudaliez et al. |
| 7,112,320 B1 | 9/2006 | Beaulieu et al. |
| 7,175,614 B2 | 2/2007 | Gollier et al. |
| 7,179,951 B2 | 2/2007 | Krishnaswamy-Mirle et al. |
| 7,202,341 B2 | 4/2007 | McGinnis et al. |
| 7,249,880 B2 | 7/2007 | Zambaux |
| 7,343,696 B2 | 3/2008 | Covert |
| 7,358,039 B2 | 4/2008 | Fischer et al. |
| 7,363,726 B2 | 4/2008 | Wang |
| 7,411,038 B2 | 8/2008 | Haynie |
| 7,422,726 B2 | 9/2008 | Hammerstedt et al. |
| 7,435,795 B2 | 10/2008 | McGinnis et al. |
| 7,473,246 B2 | 1/2009 | Vancaillie et al. |
| 7,480,032 B2 | 1/2009 | Braig et al. |
| 7,482,020 B2 | 1/2009 | Hennessy et al. |
| 7,501,493 B2 | 3/2009 | Roser |
| 7,569,184 B2 | 8/2009 | Wandell et al. |
| 7,618,406 B2 | 11/2009 | Roger |
| 7,678,888 B2 | 3/2010 | Friedman et al. |
| 7,727,743 B2 | 6/2010 | Bardat et al. |
| 7,776,022 B2 | 8/2010 | McCarthy et al. |
| 7,811,558 B2 | 10/2010 | Ho et al. |
| 7,879,332 B2 | 2/2011 | Zurlo et al. |
| 7,931,919 B2 | 4/2011 | Bakaltcheva et al. |
| 7,966,746 B2 | 6/2011 | Py |
| 8,013,022 B2 | 9/2011 | DeAngelo et al. |
| 8,057,872 B2 | 11/2011 | Chen |
| 8,097,403 B2 | 1/2012 | Ho et al. |
| 8,187,475 B2 | 5/2012 | Hecker et al. |
| 8,235,965 B2 | 8/2012 | Roger |
| 8,236,355 B2 | 8/2012 | Eijkenboom |
| 8,268,362 B2 | 9/2012 | Braun et al. |
| 8,277,837 B2 | 10/2012 | Fischer et al. |
| 8,313,654 B2 | 11/2012 | Piazza et al. |
| 8,372,343 B2 | 2/2013 | Goldstein |
| 8,377,882 B2 | 2/2013 | Schneider |
| 8,407,912 B2 | 4/2013 | Hubbard, Jr. et al. |
| 8,430,970 B2 | 4/2013 | Swami et al. |
| 8,449,520 B2 | 5/2013 | Pepper et al. |
| 8,450,079 B2 | 5/2013 | Kovalenko et al. |
| 8,491,178 B2 | 7/2013 | Breidenthal et al. |
| 8,492,081 B2 | 7/2013 | Nichols et al. |
| 8,492,087 B2 | 7/2013 | Suematsu et al. |
| 8,512,754 B2 | 8/2013 | Needham |
| 8,516,714 B2 | 8/2013 | Biemans et al. |
| 8,518,452 B2 | 8/2013 | Bjornstrup et al. |
| 8,529,961 B2 | 9/2013 | Campbell et al. |
| 8,598,319 B2 | 12/2013 | Michel et al. |
| 8,603,063 B2 | 12/2013 | Grimm |
| 8,858,681 B2 | 10/2014 | Harp |
| 8,951,565 B2 | 2/2015 | McCarthy |
| 9,011,846 B2 | 4/2015 | Overholser et al. |
| 9,046,303 B2 | 6/2015 | Yagi |
| 9,132,206 B2 | 9/2015 | McCarthy |
| 9,161,527 B2 | 10/2015 | Cutting et al. |
| 9,469,835 B2 | 10/2016 | Bronshtain |
| 9,545,379 B2 | 1/2017 | Liu et al. |
| 9,561,184 B2 | 2/2017 | Khan et al. |
| 9,561,893 B2 | 2/2017 | Root et al. |
| 9,696,284 B2 | 7/2017 | Rannisto et al. |

(56) References Cited

U.S. PATENT DOCUMENTS

| | | |
|---|---|---|
| 9,796,273 B2 | 10/2017 | Ragazzini |
| 9,863,701 B2 | 1/2018 | Robinson |
| 10,058,091 B2 | 8/2018 | Wolf et al. |
| 10,377,520 B2 | 8/2019 | Root et al. |
| 10,492,507 B2 | 12/2019 | Rizvi |
| 10,507,165 B2 | 12/2019 | Di Naro |
| 10,539,367 B2 | 1/2020 | Corbin, III et al. |
| 10,723,497 B2 | 7/2020 | Diaz Guerrero |
| 10,793,327 B2 | 10/2020 | Weimer |
| 10,830,535 B2 | 11/2020 | Oprins et al. |
| 10,844,366 B2 | 11/2020 | Durance et al. |
| 11,236,942 B2 | 2/2022 | Christ |
| 11,236,943 B2 | 2/2022 | Christ |
| 11,609,043 B2 * | 3/2023 | Johnson .................... F26B 5/06 |
| 2001/0004641 A1 | 6/2001 | Hawkins |
| 2001/0031721 A1 | 10/2001 | Webb et al. |
| 2002/0035354 A1 | 3/2002 | Mirle et al. |
| 2002/0146409 A1 | 10/2002 | Herring et al. |
| 2003/0065149 A1 | 4/2003 | McGinnis et al. |
| 2003/0068416 A1 | 4/2003 | Burgess et al. |
| 2003/0080056 A1 | 5/2003 | Boos et al. |
| 2003/0104508 A1 | 6/2003 | Gempeler et al. |
| 2003/0134418 A1 | 7/2003 | Mitaka |
| 2003/0143566 A1 | 7/2003 | Helftenbein |
| 2004/0005310 A1 | 1/2004 | Rapp et al. |
| 2004/0081588 A1 | 4/2004 | Hammerstedt et al. |
| 2004/0126880 A1 | 7/2004 | Manders et al. |
| 2004/0132207 A1 | 7/2004 | Arima et al. |
| 2005/0158856 A1 | 7/2005 | Edelson et al. |
| 2005/0170068 A1 | 8/2005 | Roodink et al. |
| 2005/0282734 A1 | 12/2005 | Kadima et al. |
| 2006/0004189 A1 | 1/2006 | Gandy |
| 2006/0134084 A1 | 6/2006 | Wolkers et al. |
| 2006/0182652 A1 | 8/2006 | Burgess et al. |
| 2006/0216687 A1 | 9/2006 | Alves-Filho et al. |
| 2006/0263759 A1 | 11/2006 | Alves-Filho et al. |
| 2007/0014780 A1 | 1/2007 | Woolverton |
| 2007/0110817 A1 | 5/2007 | Shestakov |
| 2007/0116599 A1 | 5/2007 | Walters et al. |
| 2007/0135343 A1 | 6/2007 | Webb et al. |
| 2007/0166389 A1 | 7/2007 | Bakaltcheva |
| 2007/0275028 A1 | 11/2007 | Barry et al. |
| 2008/0038818 A1 | 2/2008 | Natan et al. |
| 2008/0063697 A1 | 3/2008 | Bedard |
| 2008/0119818 A1 | 5/2008 | Bakaltcheva et al. |
| 2008/0145444 A1 | 6/2008 | Merchant et al. |
| 2008/0193386 A1 | 8/2008 | Yoo et al. |
| 2008/0206293 A1 | 8/2008 | Toreki et al. |
| 2008/0234653 A1 | 9/2008 | McCarthy et al. |
| 2008/0234654 A1 | 9/2008 | McCarthy et al. |
| 2008/0249499 A1 | 10/2008 | Vancaillie et al. |
| 2008/0256822 A1 | 10/2008 | Suzuki et al. |
| 2008/0299212 A1 | 12/2008 | Kim et al. |
| 2009/0036862 A1 | 2/2009 | Grimm |
| 2009/0107001 A1 | 4/2009 | McCarthy |
| 2009/0113753 A1 | 5/2009 | Pepper et al. |
| 2009/0223080 A1 | 9/2009 | McCarthy et al. |
| 2009/0324929 A1 | 12/2009 | Yamakawa et al. |
| 2010/0049156 A1 | 2/2010 | Dickhorner et al. |
| 2010/0144595 A1 | 6/2010 | Bucci |
| 2010/0159023 A1 | 6/2010 | Bjornstrup et al. |
| 2010/0168018 A1 | 7/2010 | Pikal et al. |
| 2011/0008458 A1 | 1/2011 | Gandy et al. |
| 2011/0008459 A1 | 1/2011 | Marguerre et al. |
| 2011/0020299 A1 | 1/2011 | Bader |
| 2011/0114524 A1 | 5/2011 | Eibl |
| 2011/0142948 A1 | 6/2011 | Langer et al. |
| 2011/0144613 A1 | 6/2011 | Pepper et al. |
| 2011/0177541 A1 | 7/2011 | Martinoli et al. |
| 2011/0183311 A1 | 7/2011 | Ho et al. |
| 2011/0263408 A1 | 10/2011 | Suto et al. |
| 2011/0282325 A1 | 11/2011 | Gregory |
| 2012/0027867 A1 | 2/2012 | Fischer et al. |
| 2012/0040384 A1 | 2/2012 | Stangier |
| 2012/0045518 A1 | 2/2012 | Nielsen et al. |
| 2012/0070855 A1 | 3/2012 | Mirshahi et al. |
| 2012/0141595 A1 | 6/2012 | Tseng et al. |
| 2012/0156306 A1 | 6/2012 | Weissman et al. |
| 2012/0231485 A1 | 9/2012 | Onundarson et al. |
| 2012/0252044 A1 | 10/2012 | Rechner et al. |
| 2012/0329082 A1 | 12/2012 | Viola et al. |
| 2013/0008048 A1 | 1/2013 | Patel et al. |
| 2013/0019572 A1 | 1/2013 | Beator et al. |
| 2013/0030161 A1 | 1/2013 | Anitua Aldecoa |
| 2013/0040890 A1 | 2/2013 | Guo et al. |
| 2013/0090291 A1 | 4/2013 | Gulle et al. |
| 2013/0116410 A1 | 5/2013 | Ivarsson et al. |
| 2013/0122107 A1 | 5/2013 | Bakaltcheva |
| 2013/0126370 A1 | 5/2013 | DiLiberto et al. |
| 2013/0143198 A1 | 6/2013 | Sailliol |
| 2013/0149727 A1 | 6/2013 | Aygen |
| 2013/0183661 A1 | 7/2013 | Prante et al. |
| 2013/0195897 A1 | 8/2013 | Teschner et al. |
| 2013/0195959 A1 | 8/2013 | Patel |
| 2013/0202585 A1 | 8/2013 | Bardat et al. |
| 2013/0243877 A1 | 9/2013 | Haley et al. |
| 2013/0251695 A1 | 9/2013 | Farmer et al. |
| 2013/0303842 A1 | 11/2013 | Zeitels et al. |
| 2013/0316011 A1 | 11/2013 | Ahn et al. |
| 2013/0326899 A1 | 12/2013 | Yagi |
| 2014/0178513 A1 | 6/2014 | Matthews |
| 2014/0212895 A1 | 7/2014 | Lim |
| 2014/0259724 A1 | 9/2014 | McCarthy et al. |
| 2014/0287643 A1 | 9/2014 | Nozaki et al. |
| 2014/0360891 A1 | 12/2014 | Kline et al. |
| 2015/0158652 A1 | 6/2015 | Root et al. |
| 2015/0354894 A1 | 12/2015 | Corbin, III et al. |
| 2016/0084572 A1 | 3/2016 | Khan et al. |
| 2016/0375184 A1 | 12/2016 | Albert et al. |
| 2017/0100339 A1 | 4/2017 | Liu et al. |
| 2017/0113824 A1 | 4/2017 | Root et al. |
| 2017/0203871 A1 | 7/2017 | Murto et al. |
| 2017/0258877 A1 | 9/2017 | Bare et al. |
| 2017/0259186 A1 | 9/2017 | Khan et al. |
| 2017/0367322 A1 | 12/2017 | Liu et al. |
| 2018/0128544 A1 | 5/2018 | Corbin, III et al. |
| 2018/0221418 A1 | 8/2018 | Daniel et al. |
| 2019/0000979 A1 | 1/2019 | Cleek et al. |
| 2019/0030169 A1 | 1/2019 | Ivarsson et al. |
| 2019/0142694 A1 | 5/2019 | Di Naro |
| 2020/0253826 A1 | 8/2020 | Qiu et al. |
| 2020/0288703 A1 | 9/2020 | Parakininkas |
| 2020/0289728 A1 | 9/2020 | Johnson |
| 2020/0292231 A1 | 9/2020 | Johnson |
| 2021/0016943 A1 | 1/2021 | Weimer |
| 2021/0127663 A1 | 5/2021 | Paukkonen |
| 2023/0008773 A1 * | 1/2023 | Johnson .................... A61J 1/14 |

FOREIGN PATENT DOCUMENTS

| | | |
|---|---|---|
| AU | 622133 B2 | 4/1992 |
| AU | 8165698 A | 1/2000 |
| AU | 744025 B2 | 2/2002 |
| AU | 2002326819 A1 | 4/2003 |
| AU | 2007205748 B2 | 11/2009 |
| AU | 2012205238 A1 | 8/2012 |
| BG | 64922 B1 | 9/2006 |
| CA | 745958 A | 11/1966 |
| CA | 780792 A | 3/1968 |
| CA | 787838 A | 6/1968 |
| CA | 835939 A | 3/1970 |
| CA | 843883 A | 6/1970 |
| CA | 1260389 A | 9/1989 |
| CN | 1210267 A | 3/1999 |
| CN | 1242429 A | 1/2000 |
| CN | 1376520 A | 10/2002 |
| CN | 1410537 A | 4/2003 |
| CN | 1156282 C | 7/2004 |
| CN | 1157194 C | 7/2004 |
| CN | 1162160 C | 8/2004 |
| CN | 1187616 C | 2/2005 |
| CN | 1220512 C | 9/2005 |
| CN | 1745627 A | 3/2006 |
| CN | 1250718 C | 4/2006 |

(56) References Cited

FOREIGN PATENT DOCUMENTS

| | | | |
|---|---|---|---|
| CN | 1267340 C | 8/2006 |
| CN | 1270731 C | 8/2006 |
| CN | 1281161 C | 10/2006 |
| CN | 1931025 A | 3/2007 |
| CN | 101152211 A | 4/2008 |
| CN | 101216432 A | 7/2008 |
| CN | 101299029 A | 11/2008 |
| CN | 101310728 A | 11/2008 |
| CN | 100469359 C | 3/2009 |
| CN | 101416985 A | 4/2009 |
| CN | 100531723 C | 8/2009 |
| CN | 101579356 A | 11/2009 |
| CN | 100584942 C | 1/2010 |
| CN | 101618120 A | 1/2010 |
| CN | 101167745 B | 6/2010 |
| CN | 101766252 A | 7/2010 |
| CN | 101833009 A | 9/2010 |
| CN | 101879333 A | 11/2010 |
| CN | 101893628 A | 11/2010 |
| CN | 101893639 A | 11/2010 |
| CN | 101957364 A | 1/2011 |
| CN | 101971972 A | 2/2011 |
| CN | 101347617 B | 4/2011 |
| CN | 102000022 A | 4/2011 |
| CN | 102008504 A | 4/2011 |
| CN | 102012433 A | 4/2011 |
| CN | 102050876 A | 5/2011 |
| CN | 102078306 A | 6/2011 |
| CN | 102106872 A | 6/2011 |
| CN | 101433553 B | 8/2011 |
| CN | 102207504 A | 10/2011 |
| CN | 101385855 B | 11/2011 |
| CN | 102229670 A | 11/2011 |
| CN | 102241767 A | 11/2011 |
| CN | 102250238 A | 11/2011 |
| CN | 101461939 B | 1/2012 |
| CN | 102337252 A | 2/2012 |
| CN | 102363634 A | 2/2012 |
| CN | 102426240 A | 4/2012 |
| CN | 102426258 A | 4/2012 |
| CN | 101285086 B | 5/2012 |
| CN | 102435743 A | 5/2012 |
| CN | 101830979 B | 6/2012 |
| CN | 101843335 B | 6/2012 |
| CN | 102507934 A | 6/2012 |
| CN | 102512418 A | 6/2012 |
| CN | 102524812 A | 7/2012 |
| CN | 102552154 A | 7/2012 |
| CN | 102579737 A | 7/2012 |
| CN | 102590496 A | 7/2012 |
| CN | 102590529 A | 7/2012 |
| CN | 102600074 A | 7/2012 |
| CN | 102600231 A | 7/2012 |
| CN | 102600508 A | 7/2012 |
| CN | 101899110 B | 8/2012 |
| CN | 102614219 A | 8/2012 |
| CN | 102628869 A | 8/2012 |
| CN | 102645358 A | 8/2012 |
| CN | 101816789 B | 9/2012 |
| CN | 102688200 A | 9/2012 |
| CN | 102692514 A | 9/2012 |
| CN | 101900712 B | 10/2012 |
| CN | 102327289 B | 10/2012 |
| CN | 102697581 A | 10/2012 |
| CN | 102746396 A | 10/2012 |
| CN | 102754848 A | 10/2012 |
| CN | 102327288 B | 11/2012 |
| CN | 102793053 A | 11/2012 |
| CN | 101843289 B | 12/2012 |
| CN | 102854322 A | 1/2013 |
| CN | 102866220 A | 1/2013 |
| CN | 102866255 A | 1/2013 |
| CN | 102879560 A | 1/2013 |
| CN | 101948630 B | 2/2013 |
| CN | 102908321 A | 2/2013 |
| CN | 102908368 A | 2/2013 |
| CN | 102093385 B | 3/2013 |
| CN | 102228683 B | 3/2013 |
| CN | 102240310 B | 3/2013 |
| CN | 102988974 A | 3/2013 |
| CN | 102210854 B | 4/2013 |
| CN | 103007280 A | 4/2013 |
| CN | 103039693 A | 4/2013 |
| CN | 103054816 A | 4/2013 |
| CN | 101756013 B | 5/2013 |
| CN | 103076455 A | 5/2013 |
| CN | 103113456 A | 5/2013 |
| CN | 102258780 B | 6/2013 |
| CN | 102319425 B | 6/2013 |
| CN | 102525954 B | 6/2013 |
| CN | 102274493 B | 8/2013 |
| CN | 203572189 U | 4/2014 |
| CN | 203572189 U | 4/2014 |
| CN | 106461327 A | 2/2017 |
| CN | 106461327 A | 2/2017 |
| CS | 277138 B6 | 11/1992 |
| DE | 109659 A1 | 11/1974 |
| DE | 2430447 A1 | 1/1975 |
| DE | 112775 A1 | 5/1975 |
| DE | 2617742 A1 | 6/1977 |
| DE | 2617742 A1 | 6/1977 |
| DE | 2365629 C2 | 6/1983 |
| DE | 19729778 A1 | 1/1999 |
| DE | 19729778 A1 | 1/1999 |
| DE | 69521470 T2 | 5/2002 |
| DE | 69133198 T2 | 7/2003 |
| DE | 69810755 T2 | 8/2003 |
| EP | 105923 A1 | 4/1984 |
| EP | 121868 A1 | 10/1984 |
| EP | 0157579 A2 | 10/1985 |
| EP | 0157579 A2 | 10/1985 |
| EP | 111777 B1 | 3/1987 |
| EP | 0124018 B1 | 11/1987 |
| EP | 204045 A3 | 1/1988 |
| EP | 0284249 A1 | 9/1988 |
| EP | 0284249 A1 | 9/1988 |
| EP | 0335682 A1 | 10/1989 |
| EP | 0335682 A1 | 10/1989 |
| EP | 0343596 A2 | 11/1989 |
| EP | 0343596 A2 | 11/1989 |
| EP | 206448 B1 | 11/1990 |
| EP | 215050 B1 | 2/1991 |
| EP | 445108 A1 | 9/1991 |
| EP | 392377 B1 | 2/1995 |
| EP | 593176 A3 | 3/1995 |
| EP | 752097 A1 | 1/1997 |
| EP | 485377 B1 | 5/1999 |
| EP | 1021726 A1 | 7/2000 |
| EP | 1087990 A1 | 4/2001 |
| EP | 1087990 A1 | 4/2001 |
| EP | 1171163 A1 | 1/2002 |
| EP | 1243275 A1 | 9/2002 |
| EP | 1286706 A2 | 3/2003 |
| EP | 876155 B1 | 7/2004 |
| EP | 1087990 B1 | 9/2004 |
| EP | 1113269 B1 | 10/2006 |
| EP | 1870649 A1 | 12/2007 |
| EP | 997735 B1 | 1/2008 |
| EP | 1958618 A1 | 8/2008 |
| EP | 1958618 A1 | 8/2008 |
| EP | 1730299 B1 | 6/2011 |
| EP | 2371343 A3 | 12/2011 |
| EP | 2431024 A1 | 3/2012 |
| EP | 2431024 A1 | 3/2012 |
| EP | 2574350 A1 | 4/2013 |
| EP | 1407780 B1 | 5/2013 |
| EP | 1407780 B1 | 5/2013 |
| EP | 2729932 A1 | 5/2014 |
| EP | 2729932 A1 | 5/2014 |
| EP | 3290064 A1 | 3/2018 |
| EP | 3290064 A1 | 3/2018 |
| FR | 2001727 A1 | 10/1969 |
| FR | 2160285 A1 | 6/1973 |
| FR | 2187909 A1 | 1/1974 |

(56) References Cited

FOREIGN PATENT DOCUMENTS

| | | |
|---|---|---|
| FR | 2224118 A1 | 10/1974 |
| FR | 2227276 A1 | 11/1974 |
| FR | 2363577 A1 | 3/1978 |
| FR | 2475737 A1 | 8/1981 |
| FR | 2600998 A1 | 1/1988 |
| FR | 2717782 A1 | 9/1995 |
| FR | 2717782 A1 | 9/1995 |
| FR | 2729932 A1 | 8/1996 |
| FR | 2729932 A1 | 8/1996 |
| FR | 2814239 A1 | 3/2002 |
| FR | 2963556 A3 | 2/2012 |
| GB | 353286 A | 7/1931 |
| GB | 425567 A | 3/1935 |
| GB | 450146 A | 7/1936 |
| GB | 450146 A | 7/1936 |
| GB | 491515 A | 9/1938 |
| GB | 620573 A | 3/1949 |
| GB | 727148 A | 3/1955 |
| GB | 731104 A | 6/1955 |
| GB | 748784 A | 5/1956 |
| GB | 748784 A | 5/1956 |
| GB | 770075 A | 3/1957 |
| GB | 807781 A | 1/1959 |
| GB | 814491 A | 6/1959 |
| GB | 814491 A | 6/1959 |
| GB | 853288 A | 11/1960 |
| GB | 859609 A | 1/1961 |
| GB | 906860 A | 9/1962 |
| GB | 911181 A | 11/1962 |
| GB | 917012 A | 1/1963 |
| GB | 941019 A | 11/1963 |
| GB | 979759 A | 1/1965 |
| GB | 1003748 A | 9/1965 |
| GB | 1073172 A | 6/1967 |
| GB | 1074461 A | 7/1967 |
| GB | 1186544 A | 4/1970 |
| GB | 1206033 A | 9/1970 |
| GB | 1206033 A | 9/1970 |
| GB | 1222810 A | 2/1971 |
| GB | 1266274 A | 3/1972 |
| GB | 1337178 A | 11/1973 |
| GB | 1372812 A | 11/1974 |
| GB | 1391746 A | 4/1975 |
| GB | 1480092 A | 7/1977 |
| GB | 1486787 A | 9/1977 |
| GB | 1486787 A | 9/1977 |
| GB | 1497517 A | 1/1978 |
| GB | 1507435 A | 4/1978 |
| GB | 1524712 A | 9/1978 |
| GB | 1530748 A | 11/1978 |
| GB | 1536725 A | 12/1978 |
| GB | 1551792 A | 8/1979 |
| GB | 1551928 A | 9/1979 |
| GB | 1563839 A | 4/1980 |
| GB | 2148090 B | 7/1987 |
| GB | 2167856 B | 12/1988 |
| GB | 2564481 A | 1/2019 |
| GB | 2564481 A | 1/2019 |
| IT | 1064142 B | 2/1985 |
| JP | S52156921 A | 12/1977 |
| JP | S53091117 A | 8/1978 |
| JP | S5426961 A | 2/1979 |
| JP | S5571452 A | 5/1980 |
| JP | S56127307 A | 10/1981 |
| JP | S56127308 A | 10/1981 |
| JP | S56160991 A | 12/1981 |
| JP | S5772911 A | 5/1982 |
| JP | S57122796 A | 7/1982 |
| JP | S57142561 A | 9/1982 |
| JP | S57159561 A | 10/1982 |
| JP | S58131566 A | 8/1983 |
| JP | S59088042 A | 5/1984 |
| JP | S59136657 A | 8/1984 |
| JP | S59181224 A | 10/1984 |
| JP | S59212768 A | 12/1984 |
| JP | S59218960 A | 12/1984 |
| JP | S60168051 A | 8/1985 |
| JP | S61040752 A | 2/1986 |
| JP | S61053567 A | 3/1986 |
| JP | S61128974 A | 6/1986 |
| JP | S61155332 A | 7/1986 |
| JP | S61225652 A | 10/1986 |
| JP | S61282054 A | 12/1986 |
| JP | S62010019 A | 1/1987 |
| JP | S62138433 A | 6/1987 |
| JP | H63-036828 A | 2/1988 |
| JP | H63-036828 A | 2/1988 |
| JP | S63157936 A | 6/1988 |
| JP | 1021741 B | 4/1989 |
| JP | H1247060 A | 10/1989 |
| JP | H2221859 A | 9/1990 |
| JP | H07270405 A | 10/1995 |
| JP | H09020687 A | 1/1997 |
| JP | H09222427 A | 8/1997 |
| JP | 2657092 B2 | 9/1997 |
| JP | H1045616 A | 2/1998 |
| JP | H10108907 A | 4/1998 |
| JP | H10-165480 A | 6/1998 |
| JP | H10165480 A | 6/1998 |
| JP | 3140797 B2 | 3/2001 |
| JP | 3142192 B2 | 3/2001 |
| JP | 3219181 B2 | 10/2001 |
| JP | 2002029977 A | 1/2002 |
| JP | 2002052067 A | 2/2002 |
| JP | 3292760 B2 | 6/2002 |
| JP | 3365091 B2 | 1/2003 |
| JP | 2003055256 A | 2/2003 |
| JP | 2003055257 A | 2/2003 |
| JP | 2003-144523 A | 5/2003 |
| JP | 2003144523 A | 5/2003 |
| JP | 2003339346 A | 12/2003 |
| JP | 2004049493 A | 2/2004 |
| JP | 3543144 B2 | 7/2004 |
| JP | 3712989 B2 | 11/2005 |
| JP | 2006036749 A | 2/2006 |
| JP | 2007197353 A | 8/2007 |
| JP | 4024506 B2 | 12/2007 |
| JP | 4059299 B2 | 3/2008 |
| JP | 2006545011-X | 5/2008 |
| JP | 2008527741 A | 7/2008 |
| JP | 2009297212 A | 12/2009 |
| JP | 2010266086 A | 11/2010 |
| JP | 2011239 A | 1/2011 |
| JP | 2011120763 A | 6/2011 |
| JP | 2012051895 A | 3/2012 |
| JP | 5002106 B2 | 8/2012 |
| JP | 5037621 B2 | 10/2012 |
| JP | 5049447 B2 | 10/2012 |
| JP | 5087815 B2 | 12/2012 |
| JP | 5252909 B2 | 7/2013 |
| JP | 5340945 B2 | 11/2013 |
| JP | 2014-028661 A | 2/2014 |
| JP | 2014-028661 A | 2/2014 |
| JP | 5960660 B2 | 8/2016 |
| JP | 2017-517335 A | 6/2017 |
| JP | 2017-517335 A | 6/2017 |
| JP | 6219922 B2 | 10/2017 |
| JP | 6305870 B2 | 4/2018 |
| JP | 2022525398 A * | 5/2022 |
| KR | 100197297 B1 | 6/1999 |
| KR | 20000020804 A | 4/2000 |
| KR | 100503629 B1 | 7/2005 |
| KR | 20060005770 A | 1/2006 |
| KR | 100631188 B1 | 10/2006 |
| KR | 100767541 B1 | 10/2007 |
| KR | 100857273 B1 | 9/2008 |
| KR | 100908742 B1 | 7/2009 |
| KR | 20110008382 A | 1/2011 |
| KR | 101157096 B1 | 6/2012 |
| KR | 101200423 B1 | 11/2012 |
| KR | 20130009161 A | 1/2013 |
| KR | 20130034991 A | 4/2013 |
| KR | 20130053609 A | 5/2013 |
| RU | 2011202 C1 | 4/1994 |

(56) References Cited

FOREIGN PATENT DOCUMENTS

| | | |
|---|---|---|
| RU | 2028130 C1 | 2/1995 |
| RU | 2028133 C1 | 2/1995 |
| RU | 2080865 C1 | 6/1997 |
| RU | 2090165 C1 | 9/1997 |
| RU | 2090166 C1 | 9/1997 |
| RU | 2121364 C1 | 11/1998 |
| RU | 2193868 C2 | 12/2002 |
| RU | 2197267 C1 | 1/2003 |
| RU | 2242759 C1 | 12/2004 |
| RU | 2266542 C1 | 12/2005 |
| RU | 2273026 C1 | 3/2006 |
| RU | 2314527 C1 | 1/2008 |
| RU | 2322243 C1 | 4/2008 |
| RU | 2332666 C1 | 8/2008 |
| RU | 2325655 C9 | 11/2008 |
| RU | 2357252 C1 | 5/2009 |
| RU | 2426548 C2 | 8/2011 |
| RU | 2442984 C1 | 2/2012 |
| RU | 2455014 C1 | 7/2012 |
| RU | 2456602 C1 | 7/2012 |
| RU | 2463063 C1 | 10/2012 |
| RU | 2012137892 A | 2/2013 |
| RU | 2478958 C1 | 4/2013 |
| RU | 2492867 C1 | 9/2013 |
| SU | 548275 A1 | 2/1977 |
| SU | 654238 A1 | 3/1979 |
| SU | 686732 A1 | 9/1979 |
| SU | 700129 A1 | 11/1979 |
| SU | 786954 A1 | 12/1980 |
| SU | 1344354 A1 | 10/1987 |
| SU | 1592717 A1 | 9/1990 |
| SU | 1678371 A1 | 9/1991 |
| SU | 1716443 A1 | 2/1992 |
| SU | 1752187 A3 | 7/1992 |
| TW | 200600103 A | 1/2006 |
| TW | I358264 B | 2/2012 |
| UA | 26543 U | 9/2007 |
| WO | WO-1992013495 A1 | 8/1992 |
| WO | WO-1992014360 A1 | 9/1992 |
| WO | WO-1995012127 A1 | 5/1995 |
| WO | WO-1995015763 A1 | 6/1995 |
| WO | 1995-027180 A1 | 10/1995 |
| WO | WO-1995-027180 A1 | 10/1995 |
| WO | 1996-029556 A1 | 9/1996 |
| WO | WO-1996-029556 A1 | 9/1996 |
| WO | 1996-031748 A1 | 10/1996 |
| WO | WO-1996-031748 A1 | 10/1996 |
| WO | WO-1997046883 A1 | 12/1997 |
| WO | 2000-036353 A1 | 6/2000 |
| WO | WO-2000-036353 A1 | 6/2000 |
| WO | WO-2000047187 A1 | 8/2000 |
| WO | WO-2001064228 A1 | 9/2001 |
| WO | WO-2002083157 A1 | 10/2002 |
| WO | WO-2002083737 A1 | 10/2002 |
| WO | WO-2002087540 A1 | 11/2002 |
| WO | WO-2003082310 A1 | 10/2003 |
| WO | 2005-089816 A1 | 9/2005 |
| WO | WO-2005089816 A1 | 9/2005 |
| WO | 2006-000422 A1 | 1/2006 |
| WO | WO-2006-000422 A1 | 1/2006 |
| WO | 2006-028648 A2 | 3/2006 |
| WO | WO-2006-028648 A2 | 3/2006 |
| WO | WO-2006054519 A1 | 5/2006 |
| WO | 2006-028648 A3 | 1/2007 |
| WO | WO-2006-028648 A3 | 1/2007 |
| WO | 2007-104760 A2 | 9/2007 |
| WO | WO-2007-104760 A2 | 9/2007 |
| WO | WO-2007104760 A3 | 4/2008 |
| WO | 2008-115548 A2 | 9/2008 |
| WO | WO-2008-115548 A2 | 9/2008 |
| WO | WO-2008108549 A1 | 9/2008 |
| WO | 2008-130602 A1 | 10/2008 |
| WO | WO-2008-130602 A1 | 10/2008 |
| WO | 2010-019217 A1 | 2/2010 |
| WO | WO-2010-019217 A1 | 2/2010 |
| WO | 2010-033169 A1 | 3/2010 |
| WO | WO-2010-033169 A1 | 3/2010 |
| WO | 2010-093429 A1 | 8/2010 |
| WO | WO-2010-093429 A1 | 8/2010 |
| WO | WO-2012092712 A1 | 7/2012 |
| WO | WO-2012098358 A1 | 7/2012 |
| WO | WO-2012101109 A1 | 8/2012 |
| WO | WO-2012140209 A1 | 10/2012 |
| WO | WO-2012159075 A1 | 11/2012 |
| WO | WO-2013013537 A1 | 1/2013 |
| WO | WO-2013042868 A1 | 3/2013 |
| WO | WO-2013057219 A1 | 4/2013 |
| WO | 2013-062479 A1 | 5/2013 |
| WO | WO-2013-062479 A1 | 5/2013 |
| WO | WO-2013076507 A2 | 5/2013 |
| WO | WO-2013085502 A1 | 6/2013 |
| WO | 2014-033228 A1 | 3/2014 |
| WO | WO-2014-033228 A1 | 3/2014 |
| WO | 2014-165222 A1 | 10/2014 |
| WO | WO-2014-165222 A1 | 10/2014 |
| WO | 2015-191599 A2 | 12/2015 |
| WO | WO-2015-191599 A2 | 12/2015 |
| WO | 2019-074886 A1 | 4/2019 |
| WO | WO-2019074886 A1 | 4/2019 |
| WO | WO-2020185916 A1 * | 9/2020 ........... A01N 1/0252 |
| WO | 2020-185909 A3 | 12/2020 |
| WO | 2020-242552 A1 | 12/2020 |
| WO | WO-2020185909 A3 | 12/2020 |
| WO | WO-2020242552 A1 | 12/2020 |

OTHER PUBLICATIONS

Chris Cherry, "Containment systems for freeze-drying," ISL-FD, Sep. 7, 2015.

Christopher Lee Albert Cherry, "Development of Novel Containment Systems for Freeze-Drying," a thesis submitted to Cardiff Metropolitan University, Apr. 10, 2013.

Glassberg et al., "Freeze-dried Plasma at the Point of Injury: from Concept to Doctrine," Shock, Dec. 2013, vol. 40, No. 6, pp. 444-450.

International Search Report and Written Opinion for International (PCT) Patent Application No. PCT/US2018/054943, dated Jan. 25, 2019, 14 pages.

International Search Report and Written Opinion for International (PCT) Patent Application No. PCT/US2020/022113, dated Nov. 5, 2020, 45 pages.

International Search Report and Written Opinion for International (PCT) Patent Application No. PCT/US2020/022120, dated Nov. 26, 2020, 17 pages.

International Search Report and Written Opinion, PCT/US2020/022128, dated Sep. 4, 2020.

Invitation to Pay Additional Fees for International (PCT) Patent Application No. PCT/US2020/022120, dated Oct. 1, 2020, 11 pages.

Jeffrey M. Soares, "Saving Lives with Freeze-dried Plasma," The United States Army, Nov. 27, 2017, pp. 1-5. URL: https://www.army.mil/article/197409.

Jeremy W. Cannon, M.D., "Prehospital Damage-Control Resuscitation," The New England Journal of Medicine, Jul. 26, 2018, pp. 387-388.

Notice of Allowance for U.S. Appl. No. 16/154,976, dated Jun. 12, 2020, 9 pages.

Notice of Allowance for U.S. Appl. No. 16/815,843, dated Sep. 24, 2021, 5 pages.

Notice of Allowance for U.S. Appl. No. 17/010,083, dated Feb. 3, 2022, 6 pages.

Notice of Allowance for U.S. Appl. No. 17/010,083, dated Nov. 24, 2021, 6 pages.

Official Action (with English abstract) for Chinese Patent Application No. 201880064085.6, dated Jul. 15, 2021, 12 pages.

Official Action (with English abstract) for Chinese Patent Application No. 201880064085.6, dated Mar. 11, 2022, 9 pages.

Official Action (with English abstract) for Japanese Patent Application No. 2020-540696, dated Aug. 24, 2021, 17 pages.

(56) References Cited

OTHER PUBLICATIONS

Official Action (with English abstract) for Japanese Patent Application No. 2020-540696, dated Jan. 11, 2022, 16 pages.
Official Action for Canadian Patent Application No. 3078625, dated Jul. 16, 2021, 3 pages.
Official Action for U.S. Appl. No. 16/154,976, dated Apr. 13, 2020, 9 pages.
Official Action for U.S. Appl. No. 16/154,976, dated Dec. 20, 2019, 12 pages.
Official Action for U.S. Appl. No. 16/815,843, dated Jun. 16, 2021, 11 pages.
Official Action for U.S. Appl. No. 17/010,083, dated Jul. 28, 2021, 7 pages.
Pan et al., "Study of Banana Hydration Using Sequential Infrared Radiation Heating and Freeze-Drying," LWT—Food Science and Technology, 2008, v. 41, pp. 1944-1951.
Sperry et al., "Prehospital Plasma during Air Medical Transport in Trauma Patients at Risk of Hemorrhagic Shock," The New England Journal of Medicine, Jul. 26, 2018, pp. 315-326.
Updated Notice of Allowance for U.S. Appl. No. 17/010,083, dated Dec. 19, 2021, 2 pages.

\* cited by examiner

LYOPHILIZATION CONTAINER FILL FIXTURE, SYSTEM AND METHOD OF USE

This application is a continuation of U.S. patent application Ser. No. 16/815,904, entitled "Lyophilization Container Fill Fixture, System And Method Of Use," filed in the U.S. Patent and Trademark Office on Mar. 11, 2020, which claims the benefit of U.S. Provisional Patent Application No. 62/818,214, entitled "Multi-part Lyophilization Container and Method of Use," filed in the U.S. Patent and Trademark Office on Mar. 14, 2019, U.S. Provisional Application No. 62/952,752, entitled "Lyophilization Loading Tray Assembly and System," filed in the U.S. Patent and Trademark Office on Dec. 23, 2019, and Provisional Patent Application No. 62/971,072, entitled "Lyophilization Container Fill Fixture, System and Method of Use," filed in the U.S. Patent and Trademark Office on Feb. 6, 2020, each of which is incorporated by reference herein in its entirety.

The invention was made with government support under contract number H92222-16-C-0081 awarded by the United States Department of Defense. The government has certain rights in the invention.

BACKGROUND

The present application relates to the lyophilization of a composite fluid, such as human or animal blood or blood plasma. In particular, the present application describes a gas fill fixture for preparing a flexible lyophilization container to be used in a lyophilization process, including a related system and method. The gas fill fixture is a rigid housing configured to house a flexible lyophilization container and to provide a gas fill indication to an operator. The system includes the gas fill fixture, a lyophilization container and a lyophilizer. The method relates to the inclusion of the gas fill fixture in a lyophilization process.

Various methods for lyophilizing a fluid are known. One example of such a method is described in U.S. Application Publication No. 2019/0106245 to Weimer et al., entitled "Lyophilization Container and Method of Using Same." In the described method, a gas is added to a flexible lyophilization container which houses a fluid to be lyophilized. The gas is added to the flexible lyophilization container prior to the freezing step for the purpose of creating a vapor space above the ice cake to be formed. The inclusion of a vapor space above the formed ice cake facilitates vapor flow throughout sublimation and desorption.

At present, a simple and precise means for inputting a correct gas volume into the flexible lyophilization container does not exist. Current gas fill procedures are generally performed manually and are consequently considered to be cumbersome and imprecise. This imprecision, in turn, may result in inconsistencies in batch lyophilization processes. Accordingly, the present application describes an improvement to current devices and techniques used to perform a gas fill step in the lyophilization of a biological fluid such as blood or a blood product.

Although specific embodiments of the present application are provided in view of the above-described considerations, the specific problems discussed herein should not be interpreted as limiting the applicability of the embodiments of this disclosure in any way.

SUMMARY

This summary is provided to introduce aspects of some embodiments of the present application in a simplified form and is not intended to comprise an exhaustive list of all critical or essential elements of the claimed invention, nor is it intended to limit the scope of the claims.

In one aspect, embodiments provide for a gas fill fixture for use in lyophilization. The gas fill fixture includes a chassis, fill indicator and a lid. The chassis and lid together form a cavity configured to receive a flexible lyophilization container placed along its longitudinal axis therein.

In another aspect, embodiments provide for a system for lyophilizing a fluid. The system includes a lyophilization container, a lyophilizer and a gas fill fixture. The gas fill fixture includes a chassis, a fill indicator and a lid.

In yet another aspect, embodiments provide for a method of lyophilizing a fluid. The method includes inputting a liquid into a flexible lyophilization container, inputting a portion of the lyophilization container into a gas fill fixture, inputting a gas into the lyophilization container, determining an appropriate gas fill volume based on an indication from a fill indicator of the gas fill fixture, loading the lyophilization container into a lyophilizer and lyophilizing the fluid.

Further embodiments of the present application include additional methods and devices and systems for lyophilizing fluids. The fluid may be any suitable liquid, including human or animal plasma.

BRIEF DESCRIPTION OF THE DRAWINGS

Non-limiting and non-exhaustive embodiments are described with reference to the following figures.

DETAILED DESCRIPTION

The principles described in the present application may be further understood by reference to the following detailed description and the embodiments depicted in the accompanying drawings. Although specific features are shown and described below with respect to particular embodiments, the present application is not limited to the specific features or embodiments provided. Moreover, embodiments below may be described in association with the lyophilization of biological fluids, such as human or animal blood or blood components; however, such descriptions are merely illustrative. Those of skill in the art will appreciate that embodiments of this disclosure may be used in connection with the determining of a correct gas fill volume in many contexts.

Embodiments of the present application principally refer to a stand-alone fixture that is utilized in the preparation of a fluid to be lyophilized. More particularly, a gas fill fixture is described which allows for the placement of a flexible lyophilization container therein, and which provides an indication to an operator when a proper gas fill volume in the flexible container has been achieved.

Any suitable fluid may be prepared for lyophilization and lyophilized using the devices and techniques described in this disclosure, including a biological fluid such as human or animal blood or a blood product, such as blood plasma.

Various advantages of the enumerated embodiments are noted throughout this disclosure.

Figure 1:
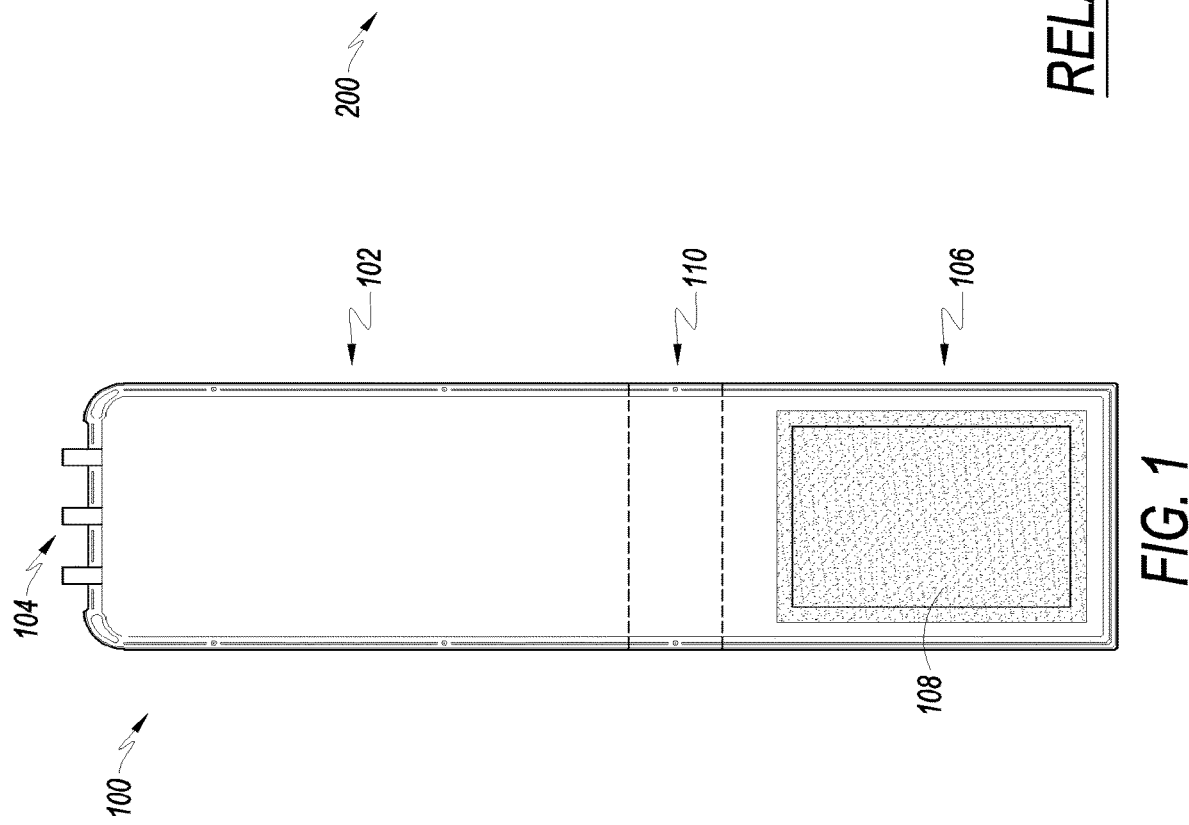
FIG. 1 is an illustration of a flexible multi-part lyophilization container according to the related art.

FIG. 1 is an illustration of a flexible multi-part lyophilization container according to the related art.

Referring to FIG. 1, the lyophilization container 100 includes a non-breathable section 102; including a port region 104; a breathable section 106, including a breathable membrane 108; and an occlusion zone 110.

In operation, lyophilization container 100 exchanges fluids via ports positioned in the port region 104 of non-breathable section 102. Fluid exchanges occur during the initial filling of the container with liquid plasma and during the post-lyophilization filling of the container with sterile water for reconstitution and transfusion into a patient. Non-breathable section 102 and breathable section 106 are isolated from one another by a peelable seal or by a creation of an occlusion of the container in the occlusion zone 110 encompassing the transition between the non-breathable section 102 and breathable section 106. In this respect, the occlusion zone (i.e., the position of the peelable seal and/or the occlusion) 110 defines the boundary between non-breathable section 102 and breathable section 106.

Figure 2:
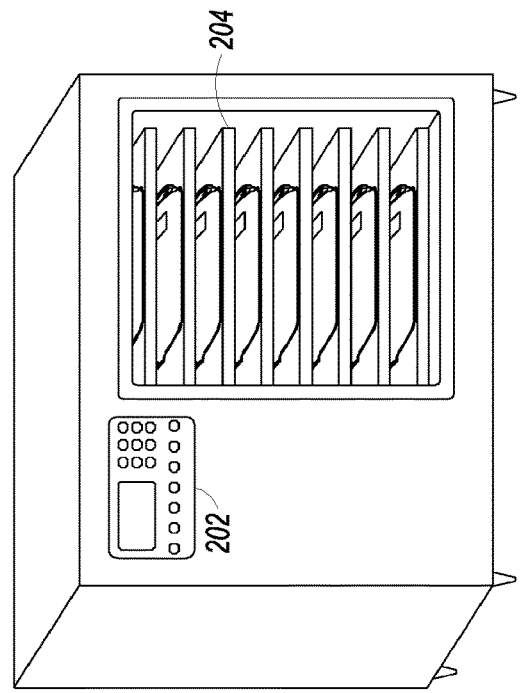
FIG. 2 is an illustration of a lyophilizer according to the related art.

FIG. 2 is an illustration of a lyophilizer according to the related art.

Referring to FIG. 2, the lyophilizer 200 comprises timing and temperature controls 202; and a hydraulic shelf system 204.

The lyophilizer shown in FIG. 2 is generic illustration of a conventional lyophilizer suitable for use in conjunction with embodiments of the present application. Typical components of suitable conventional lyophilizers include timing and temperature controls, a refrigeration system, a vacuum system, a condenser and a chamber including a hydraulic shelf system capable of lyophilization and stoppering.

Figure 3:
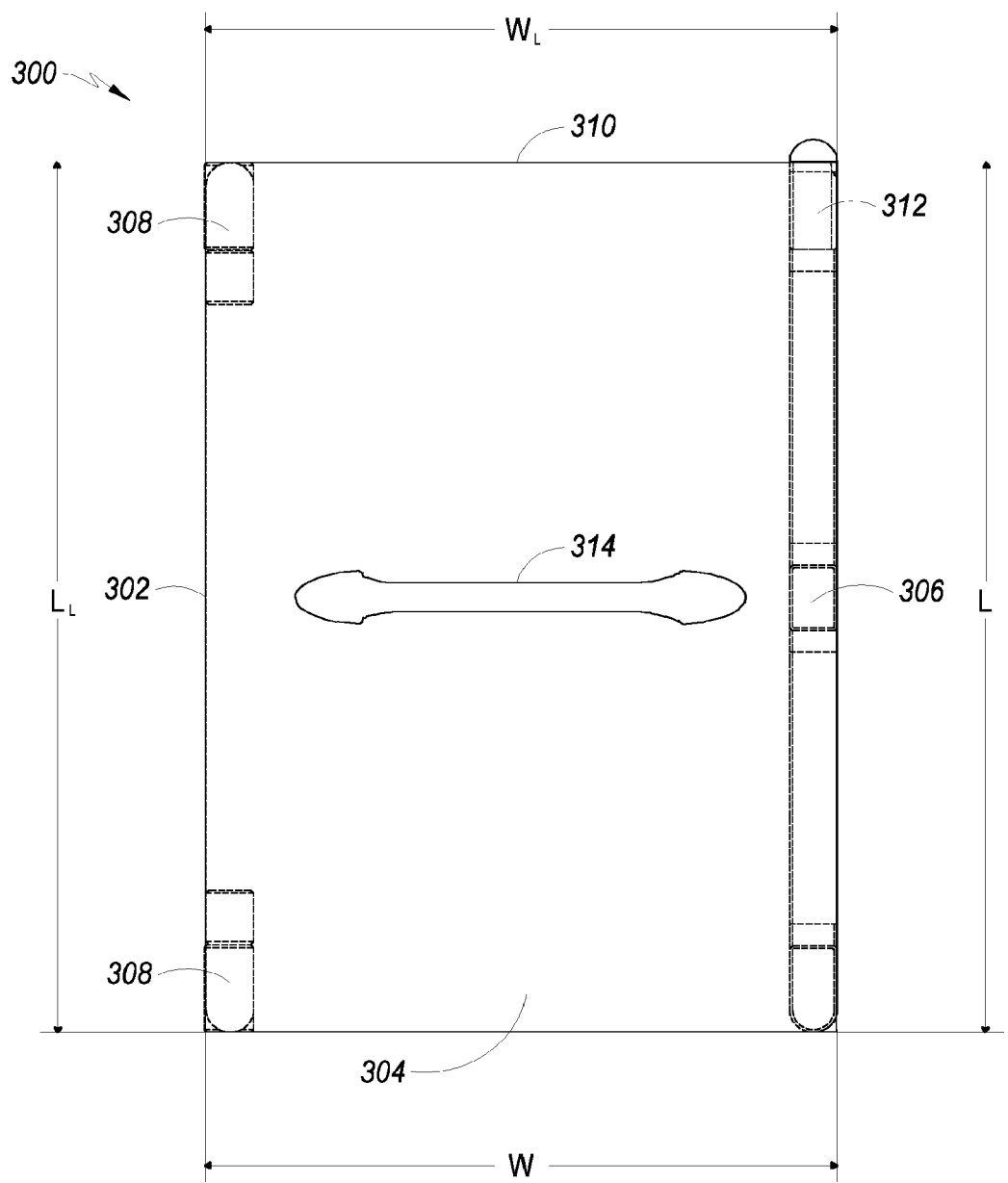
FIG. 3 is a plan view of a gas fill fixture according to an embodiment of the present application.

FIG. 3 is a plan view of a gas fill fixture according to an embodiment of the present application.

Referring to FIG. 3, gas fill fixture 300 comprises chassis 302, including platform 304, side wall 306 and hinges 308; lid 310; fill indicator 312 and handle 314.

Chassis 302 comprises platform 304, side wall 306 and hinges 308. Lid 310 is attached to chassis 302 via hinges 308. Fill indicator 312 and handle 314 are respectively attached to the bottom side and to the top side of lid 310.

The length and width of chassis 302 are respectively denoted as "L" and "W". In the embodiment shown in FIG. 3, chassis 302 length is approximately 26 cm and chassis 302 width is approximately 17 cm. As shown, lid 310 length, denoted as "$L_L$," is essentially coincident to the length of the chassis 302. Lid 310 width, denoted as "$W_L$," is likewise essentially coincident to width of the chassis 302.

In embodiments, neither the size and shape of the chassis 302 or the lid 310, nor their relationship to one another, are limited. For example, chassis 302 length may be between 15 cm and 50 cm, such as between 25 cm and 30 cm, and chassis width may be between 10 cm and 30 cm, such as between 15 cm and 20 cm. Similarly, lid 310 length may be between 15 cm and 50 cm, such as between 25 cm and 30 cm and lid 310 width may be between 10 cm and 30 cm, such as between 15 and 20 cm.

In the embodiment shown in FIG. 3, platform 304, side wall 306 and hinges 308 comprise a blend of Polycarbonate (PC) and Acrylonitrile Butadiene Styrene (ABS). PC/ABS is preferable for its toughness and impact resistance. Platform 304 is a solid piece of PC/ABS, whereas side wall 306 and hinges 308 are injection molded and cored using conventional techniques to reduce mass. Lid 310 is a transparent thermoplastic (e.g., acrylic). Thermoplastic is preferable for its durability and low cost. Transparency allows an operator to visually inspect the lyophilization container throughout a gas fill process.

In the embodiment of FIG. 3, hinges 308 are a type of pivot hinge. Each hinge 308 comprises a top and a bottom hinge mount respectively attached to lid 310 and to platform 314. Each of the top and the bottom hinge 308 mount comprises a cup configured to house a portion of a dowel forming a pivotal connection therebetween. Alternative embodiments are not limited and may include a variety of conventional hinges, such as alternative pivot hinges, a metal butt hinge or Mortise hinge. Fill indicator 312 is a mechanical gauge configured to provide an operator with a means to visually determine a correct gas fill volume of an inputted lyophilization container. Handle 314 is plastic and resembles a conventional cabinet door pull or drawer pull.

A variety of alternative materials may be used in the individual components of the gas fill fixture 300. Any material selected should be resilient under repeated use conditions, including but not limited to plastics, metals, and metal alloys. In a preferred embodiment, fixture components are attached to one another with conventional screws; however, fixture components may be attached or adhered to one another using any other conventional technique, hardware, adhesive or the like.

In various alternative embodiments, a bumper or similar implement may be positioned between the side wall 306 and the lid 310 to absorb the shock of lid 310 closures, thereby prolonging fixture 300 lifespan. Such bumper embodiments may comprise any of a variety of materials, including but not limited to a high-density synthetic rubber such as Ethylene Propylene Diene Monomer rubber (EPDM). Material selected for use in a bumper should be shock absorbent and durable.

Figure 4A:
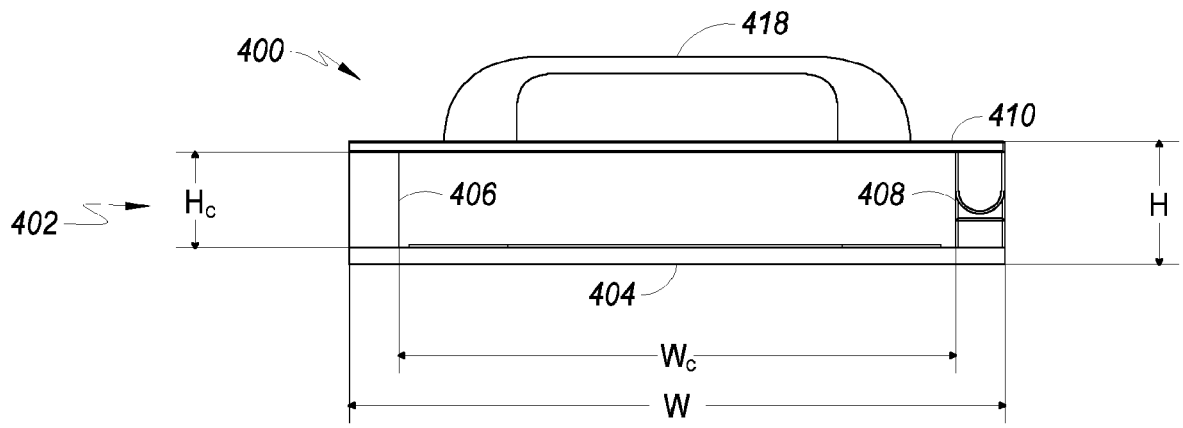
FIGS. 4A to 4C are front views of a gas fill fixture according to an embodiment of the present application.
Figure 4B:
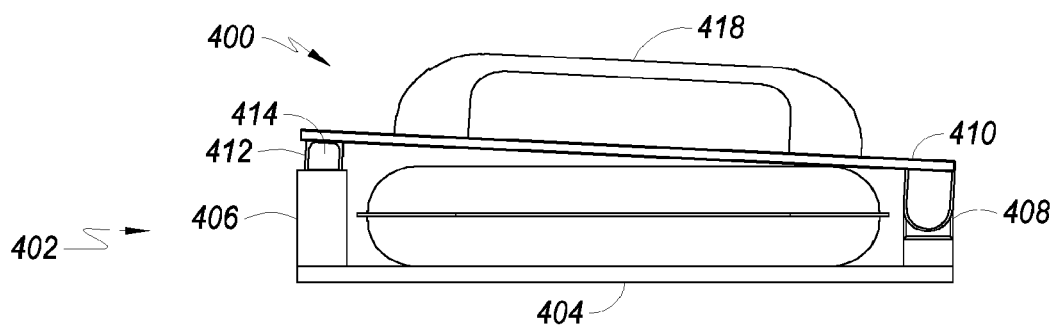
Figure 4C:
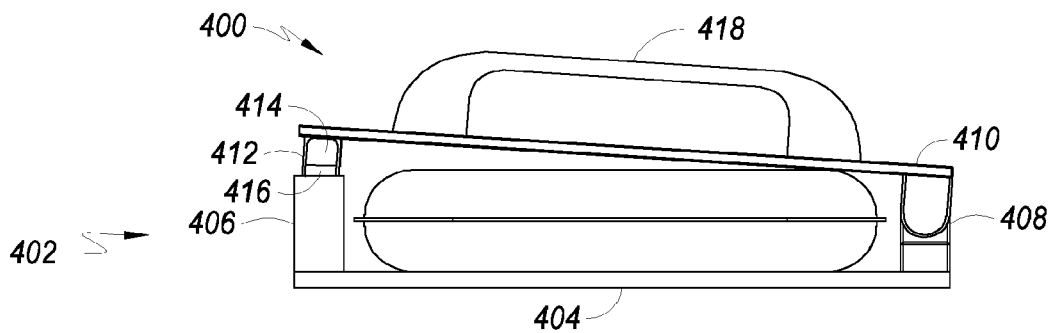

FIGS. 4A to 4C are front views of a gas fill fixture according to an embodiment of the present application.

Referring to FIGS. 4A to 4C, gas fill fixture 400 comprises chassis 402, including platform 404, side wall 406 and hinge 408; lid 410; fill indicator 412, including first indication section 414 and second indication section 416; and handle 418.

FIG. 4A is in illustration of a fill fixture 400 in a closed state. FIG. 4B is an illustration of a fill fixture 400 indicating a proper fill condition. FIG. 4C is an illustration of a fill fixture 400 indicating an overfilled condition.

In the embodiments shown in FIGS. 4A to 4C, chassis 402 is constructed from platform 404, side wall 406 and hinges 408 which together support lid 410. The fixture cavity formed within the assembled components is configured to accept, along its longitudinal axis, a portion of a flexible lyophilization container to be filled with a gas.

As shown in FIG. 4A, chassis 402 width, denoted as "W" is approximately 17 cm. Each of side wall 406 width and hinge width is approximately 1.5 cm. In embodiments, however, neither of side wall 406 width nor hinge 408 width are limited and either may be between 0.5 cm and 5 cm, such as between 2 cm and 4 cm. As shown, platform 404 width is coincident with chassis width. In embodiments, however, platform 404 width is not limited and may be between 10 cm and 30 cm, such as between 15 cm and 20 cm. In yet further embodiments having a differently configured chassis, platform 404 width may not be coincident to chassis width.

Overall fixture 400 height denoted as "H" is approximately 3.5 cm. In embodiments, however, fixture height is not limited and may be between 2 cm and 8 cm, such as between 3 cm and 5 cm. Overall fixture height includes lid 410 thickness and platform 404 thickness. As shown, each of lid 410 thickness and platform 404 thickness is approximately 0.5 cm. In embodiments, however, neither lid 410 thickness nor platform 404 thickness are limited, and either may be between 0.1 cm and 1 cm, such as between 0.3 cm and 0.7 cm. Side wall 406 height and hinge 408 height are each approximately 2.5 cm. In embodiments, however, neither side wall 406 height nor hinge 408 height is limited and either may be between 1 cm and 5 cm, such as between 2 cm and 3 cm.

Internal cavity height, denoted as "$H_C$," is approximately 2.5 cm. In embodiments, internal cavity height is not limited and may be between 2 cm and 6 cm, such as between 3 cm and 5 cm. As shown in FIG. 4, internal cavity height is coincident to the side wall height and to hinge 408 height; however, in alternative embodiments comprising a differently configured chassis, internal cavity height may not be coincident to side wall 406 height or hinge 408 height. Internal cavity width, denoted as "$W_C$," is approximately 14 cm. In embodiments, however, internal cavity width is not limited and may be between 8 cm and 20 cm, such as between 12 cm and 16 cm. Internal cavity length, although not shown, is generally coincident to chassis length and, in embodiments, may vary accordingly. In embodiments, any of the fixture dimensions, including their relationship to one another, are not limited and may vary.

As described below and shown in FIGS. 4A to 4C, fill indicator 412 is a vertically oriented, linear indicator attached to the bottom side of lid 410. Fill indicator 412 may be considered a conventional go/no-go gauge including a first indication section 414 and second indication section 416; the first section indicating a proper fill condition and the second section indicating an overfilled condition. In alternative embodiments; however, the location and configuration of fill indicator 412 is not limited and may vary without departing from the scope of this application.

FIG. 4A illustrates fill fixture 400 in a closed position. That is, lid 410 is at rest on chassis 402, and the fill indicator 412 remains obstructed from view behind an end portion of sidewall 406. In this closed position, fill indicator 412 does not indicate any fill condition.

FIG. 4B is an illustration of a fill fixture 400 indicating a proper fill condition. That is, a flexible lyophilization container has been placed within the fixture cavity and filled with a gas. Consequently, lid 410 has been lifted, and a first indication section 414 of fill indicator 412 configured to indicate that the lyophilization container has been filled with a desired amount of gas has been exposed. In exemplary embodiments, the color green is used to indicate a proper fill condition. However, in alternative embodiments, the type of visual indicator used for the first indication section is not limited and may be any suitable visual indicator such as another color, a conspicuous texture, or the like.

FIG. 4C illustrates fill fixture 400 in an overfilled condition. That is, a flexible lyophilization container has been placed within the fixture cavity and overfilled with a gas. Consequently, lid 410 has been lifted beyond a proper fill condition, exposing a second indication section 416 of fill indicator 412 designed to indicate that the lyophilization container has been filled with an amount of gas in excess of a desired amount. In exemplary embodiments, the color red is used to indicate an overfilled condition. However, in alternative embodiments, the type of visual indicator used for the second indication section is not limited and any suitable visual indicator that is dissimilar to the indicator used for a proper fill condition may be used. For example, another color, a different texture, or the like may be used to indicate an overfilled condition.

In embodiments, chassis 402 may include components comprising dissimilar materials. For instance, platform 404 may comprise plastic whereas side wall 406 and hinges 408 may comprise a metal or vice versa. In further embodiments, platform 404 and side wall 406 may be formed as a single component. Various additional material choices and design combinations are within the scope of this application and can be readily envisioned by one of skill in the art.

As shown in FIGS. 4A to 4C, handle 418 resembles a conventional cabinet door pull or drawer pull. Handle 418 may be sized to allow an operator to manipulate lid 410 with a bare hand or with a gloved hand. Handle 418 is disposed at approximately the center of lid 410, perpendicular to the longitudinal axis of the fixture 400 cavity. In this configuration, it is possible to load a portion of a flexible lyophilization container into the fixture cavity along its longitudinal axis and to fold the remainder of the flexible container over the edge of the lid 410 in a manner allowing the remainder of the flexible container to be secured in the void space of the handle 418 (See FIG. 6). In such embodiments, specialized features such as cutouts, indentations or any other suitable features may be incorporated into the flexible container to cooperate with the handle 418 in securing the container. The ability to secure the entire flexible container to the fill fixture 400 in this manner may simplify the process of obtaining an accurate weight of the combined fixture and container before a fill procedure.

Figure 5:
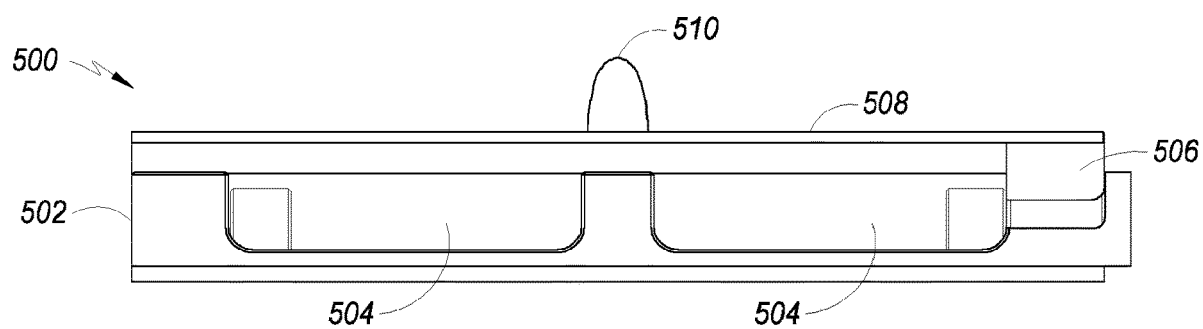
FIG. 5 is a side view of a gas fill fixture according to an embodiment of the present application.

FIG. 5 is a side view of a gas fill fixture according to an embodiment of the present application.

Referring to FIG. 5, gas fill fixture 500 comprises side wall 502, including cutout portions 504; fill indicator 506; lid 508; and handle 510.

As shown, when the lid 508 is in the closed position, the fill indicator 506 rests adjacent to, and at a minimal distance from, a portion of side wall 502. Maintaining a minimal distance between the fill indicator 506 and the side wall 502 portion allows only one fill indication section of the fill indicator 506 to be visible to an operator at a given fill condition, thereby reducing the potential for operator error. Notably, side wall 502 includes cutout portions 504 to reduce mass and to reduce cost.

In further embodiments, fill indicator 506 may be differently configured and may include various alternative or additional technologies. For example, fill indicator 506 may be incorporated into one or more fixture components, and may comprise one or more of a camera, a sensor, a light or any other conventional electrical or mechanical means of providing a visual indication or performing visual or electronic monitoring or inspection of the gas fill process. The particular type of camera, sensor or light is not limited. For instance, an included sensor may be selected from among any of optical sensors, inductive sensors or capacitive sensors.

Figure 6:
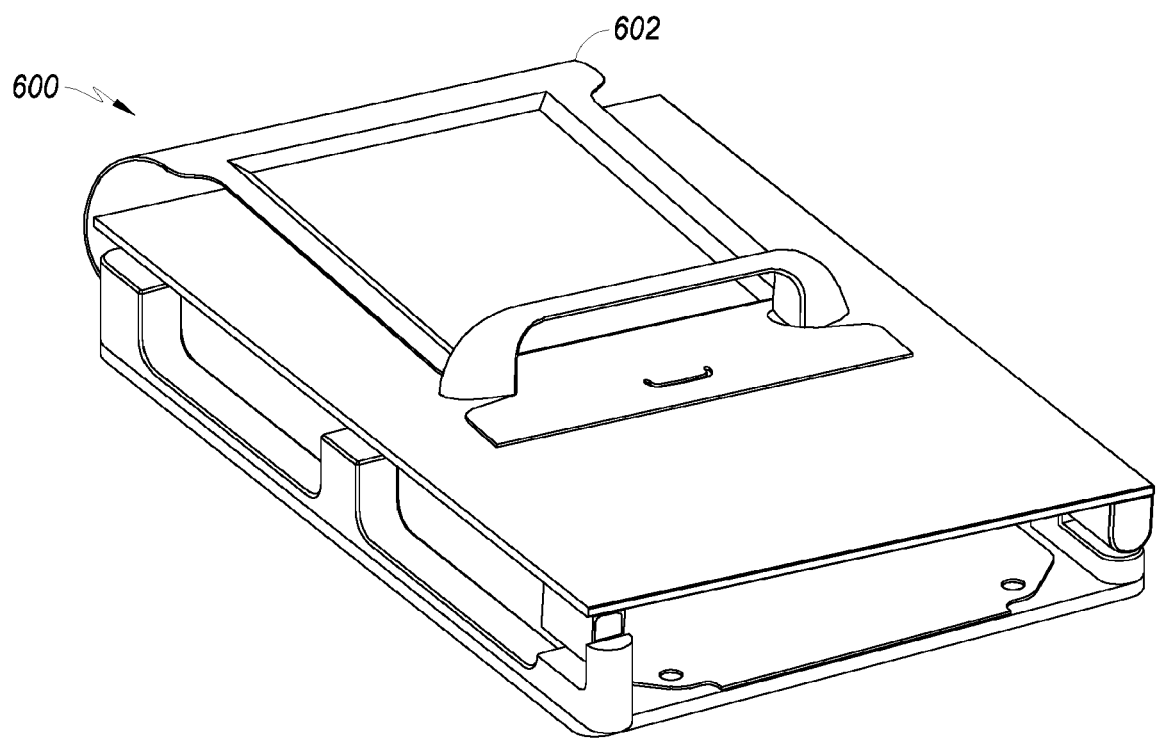
FIG. 6 is perspective view of a gas fill fixture housing a flexible lyophilization container according to an embodiment of the present application.

FIG. 6 is perspective view of a gas fill fixture housing a flexible multi-part lyophilization container according to an embodiment of the present application.

Referring to FIG. 6, gas fill fixture 600 is shown accommodating a flexible, multipart lyophilization container 602.

As shown, a non-permeable portion of the lyophilization container 602 has been loaded into the fixture 600 cavity and filled with a gas. Accordingly, the lid is shown as having been lifted from the chassis, allowing the fill indicator to extend upward and indicate a proper fill condition. A portion of the lyophilization container 602 including a gas permeable membrane has been folded over the lid of the gas fill fixture 600 and secured in the void space of the handle. The securing of the lyophilization container 602 in the handle is achieved by a cooperation between lyophilization container 602 features and complementary features of the fixture handle.

The fill fixture 600 assists an operator in the creation of a desired vapor space in the lyophilization container 602 to reduce the amount of ice "sticking" to the container material during and after the freezing step of lyophilization. Material and design choices should take into consideration that the creation of a vapor space in the lyophilization container 602 may cause container pressure to reach between 0.3 Pound per square inch (Psi) and 1.0 Psi, such as 0.5 Psi (approximately 26 mmHG).

Figure 7:
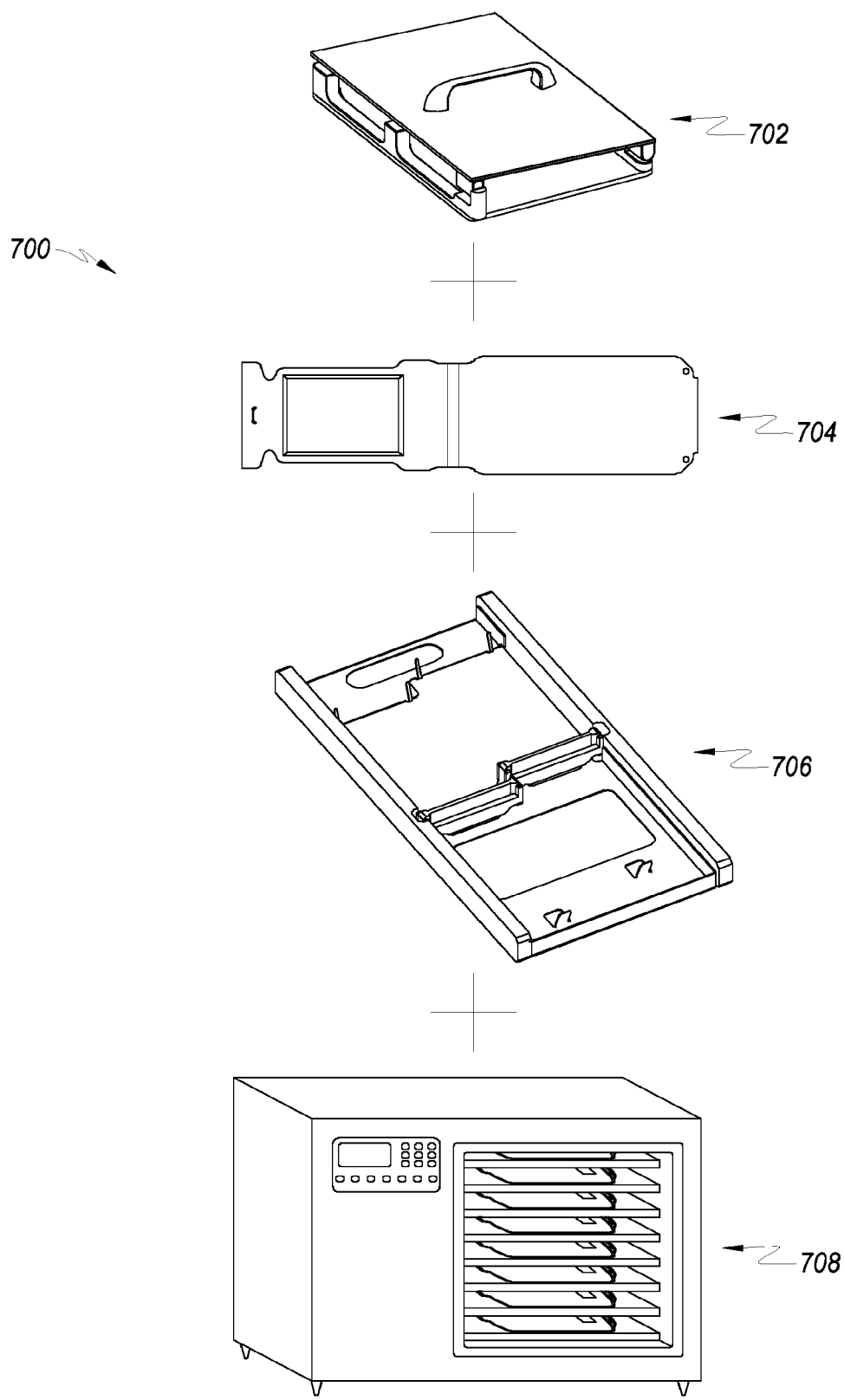
FIG. 7 is an illustration of a system for lyophilizing a fluid according to an embodiment of the present application.

FIG. 7 is an illustration of a system for lyophilizing a fluid according to an embodiment of the present application.

Referring to FIG. 7, the system 700 includes a gas fill fixture 702; a lyophilization container 704; a lyophilization loading tray 706; and a lyophilizer 708.

System 700 may vary in embodiments. For example, system 700 may exclude the lyophilization loading tray 706 altogether. In other embodiments, system 700 may employ components that are differently configured than those shown. For instance, lyophilizer 708 may be used in conjunction with a freezer that is a separate system component. Similarly, an alternatively configured lyophilization container 704 may result in differently configured system components which is within the scope of this application and can be readily envisioned by one of skill in the art. In yet further embodiments, various positioning and securing features may be incorporated into system components to ensure the proper positioning and securing of the lyophilization container to each system component.

An exemplary workflow included below describes the manner in which embodiments of the gas fill fixture may be included in a lyophilization process.

Figure 8:
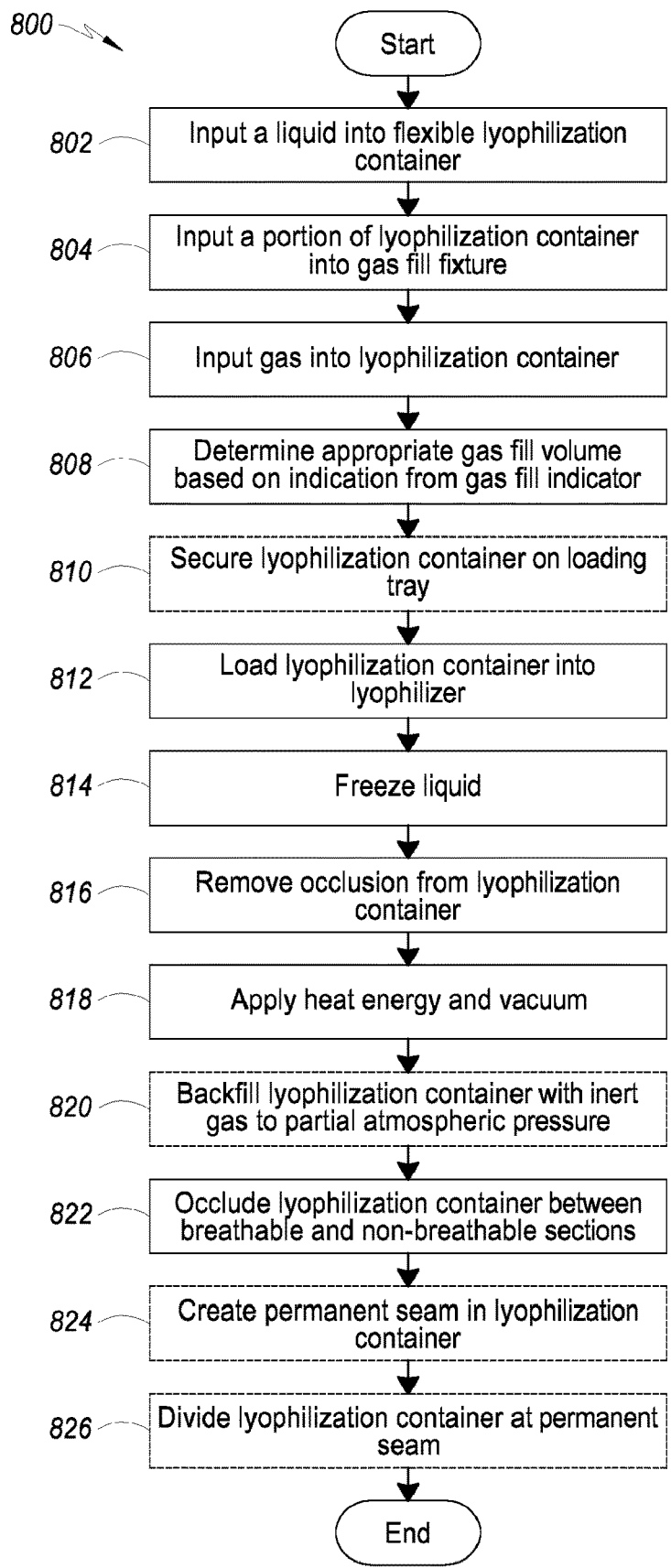
FIG. 8 is a workflow schematic illustrating a lyophilization process according to an embodiment of the present application.

FIG. 8 is workflow schematic illustrating a lyophilization process according to an embodiment of the present application.

Referring to FIG. 8, in step 802, a subject fluid (e.g., blood plasma) is inputted into a non-breathable section of a flexible lyophilization container. In step 804, the non-breathable section of the lyophilization container is loaded into a gas fill fixture. In step 806, a gas is inputted into the non-breathable section of the lyophilization container. In step 808, an appropriate gas fill volume is determined based on a proper fill indication from fill indicator of the gas fill fixture. In this step, the gas is preferably Nitrogen; however, an alternative gas may be introduced, such as air, another inert gas, or a pH regulating gas, e.g., $CO_2$. In step 810, the lyophilization container is optionally attached to a loading tray or other loading apparatus. In step 812, the lyophilization container is loaded into to a lyophilizer. In step 814, the liquid in the lyophilization container is frozen, creating a thin, uniformly thick structure of ice in the non-breathable section. In step 816, an occlusion is removed from the lyophilization container, allowing a pathway to exist between the non-breathable section of the lyophilization container and a breathable section of the lyophilization container. In this step, the removal of the occlusion may comprise, e.g., the opening of a peelable seal or the release of a mechanical clamp. In step 818, vacuum and heat energy are applied to accomplish sublimation and desorption, causing a phase change in the ice structure from the solid phase directly to the vapor phase. Vapor released from the ice structure flows through the lyophilization container cavity via the created pathway and escapes through the breathable section of the lyophilization container, leaving a lyophilized plasma cake in the non-breathable section. In step 820, the lyophilization container is optionally backfilled with an inert gas to raise lyophilization container pressure to partial atmospheric pressure. In step 822, the lyophilization container is occluded, dividing the non-breathable section from the breathable section in order to prevent contamination of the lyophilizate. In step 824, a permanent seam is optionally created in the non-breathable material of the lyophilization container. In step 826, the lyophilization container is optionally divided at the permanent seam, leaving the lyophilized end-product in the non-breathable section.

Notwithstanding the various specific embodiments enumerated in this disclosure, those skilled in the art will appreciate that a variety of modifications and optimizations could be implemented for particular applications without departing from the scope of this application. For instance, in alternative embodiments, the fill fixture may be adapted to fill multiple lyophilization containers simultaneously. Likewise, the fixture may be configured to accommodate the unique dimensions of any particular lyophilization container. In yet further embodiments, the gas fill fixture and other system components may include tabs, pins, clips or any other conventional attachment means configured to secure the lyophilization container in the correct position. Additionally, the present application is not limited to the lyophilization of blood or blood products. That is, the principles of the present application may be applicable to the lyophilization of many fluids. Accordingly, various modifications and changes may be made in the arrangement, operation, and details of the methods and systems of the present application which will be apparent to those skilled in the art.

What is claimed is:

1. A fluid fill indicator for a lyophilization assembly, the fluid fill indicator comprising:
   a chassis;
   a lid; and
   a fill indicator fixed to a surface of the lid and configured to indicate a fill position based on a position of the lid relative to the chassis, the fill indicator configured to receive a lyophilization container that is configured to be received by a lyophilizer.

2. The fluid fill indicator of claim 1, wherein the chassis includes Acrylonitrile Butadiene Styrene (ABS).

3. The fluid fill indicator of claim 1, wherein the chassis includes Polycarbonate (PC).

4. The fluid fill indicator of claim 1, wherein the lid is movably fixed to the chassis by a hinge.

5. The fluid fill indicator of claim 4, wherein the hinge is a pivot hinge.

6. The fluid fill indicator of claim 1, wherein the lid includes a handle.

7. The fluid fill indicator of claim 1, wherein the fill indicator is disposed in a corner of the lid.

8. The fluid fill indicator of claim 1, wherein the fill indicator is a mechanical indicator.

9. The fluid fill indicator of claim 8, wherein the mechanical indicator is a linear indicator.

10. The fluid fill indicator of claim 9, wherein the linear indicator uses multiple colors to indicate a proper fill condition and an overfilled condition.

11. The fluid fill indicator of claim 1, wherein the fill indicator includes a sensor.

12. The fluid fill indicator of claim 6, wherein the sensor is selected from among optical sensors, inductive sensors, and capacitive sensors.

13. The fluid fill indicator of claim 1, wherein the fill indicator is a projection extending from a bottom surface of the lid toward the chassis.

14. The fluid fill indicator of claim 13, wherein the chassis includes a projection extending from a top surface of the chassis, and as the lid pivots, a location of the fill indicator relative to the projection on the chassis indicates the fill position.

15. A system for lyophilizing a fluid, the system comprising:
    a lyophilization tray configured to receive a lyophilization container;
    a lyophilizer configured to receive the lyophilization tray; and
    a fluid fill indicator configured to receive the lyophilization container, the fluid fill indicator including
        a chassis,
        a lid, and
        a fill indicator fixed to a surface of the lid and configured to indicate a fill position based on a position of the lid relative to the chassis.

16. The system of claim 15, wherein the fill indicator is a mechanical indicator.

17. The system of claim 16, wherein the mechanical indicator is a linear indicator.

18. The system of claim 16, wherein the linear indicator uses multiple colors to indicate a proper fill condition and an overfilled condition.

19. The system of claim 15, wherein the lid is pivotably attached to the chassis by a hinge.

20. The system of claim 15, wherein the chassis includes sidewalls defining an interior space configured to receive the lyophilization container.

* * * * *